United States Patent
Augelli et al.

(10) Patent No.: US 11,039,857 B2
(45) Date of Patent: Jun. 22, 2021

(54) CANNULA ASSEMBLY FOR ROBOTICALLY ASSISTED PRESSURE REGULATED LAPAROSCOPIC SURGICAL PROCEDURES

(71) Applicant: Conmed Corporation, Utica, NY (US)

(72) Inventors: Michael J. Augelli, Prospect, CT (US); Dominick Mastri, Bridgeport, CT (US); Kenneth Blier, Cheshire, CT (US)

(73) Assignee: Conmed Corporation, Utica, NY (US)

( * ) Notice: Subject to any disclaimer, the term of this patent is extended or adjusted under 35 U.S.C. 154(b) by 0 days.

(21) Appl. No.: 15/646,673

(22) Filed: Jul. 11, 2017

(65) Prior Publication Data

US 2018/0008313 A1 Jan. 11, 2018

Related U.S. Application Data

(60) Provisional application No. 62/360,724, filed on Jul. 11, 2016.

(51) Int. Cl.
*A61B 17/34* (2006.01)
*A61M 13/00* (2006.01)
(Continued)

(52) U.S. Cl.
CPC ...... *A61B 17/3498* (2013.01); *A61B 17/3417* (2013.01); *A61B 17/3421* (2013.01);
(Continued)

(58) Field of Classification Search
CPC . A61B 17/02; A61B 17/3498; A61B 17/3423; A61B 17/3433;
(Continued)

(56) References Cited

U.S. PATENT DOCUMENTS

| | | | |
|---|---|---|---|
| 6,123,689 | A | 9/2000 | To et al. |
| 10,492,825 | B2 | 12/2019 | Lambrecht et al. |
| 2014/0171855 | A1 | 6/2014 | Mastri et al. |
| 2014/0276946 | A1* | 9/2014 | Lambrecht ......... A61B 17/3421 606/130 |

(Continued)

FOREIGN PATENT DOCUMENTS

| | | |
|---|---|---|
| KR | 10-2015-0125668 A | 11/2015 |
| WO | WO-2014144771 A1 | 9/2014 |
| WO | WO-2016100181 A1 | 6/2016 |

OTHER PUBLICATIONS

International Search Report and Written Opinion of the International Searching Authority dated Aug. 18, 2017 in corresponding International Application No. PCT/US2017/041568.

(Continued)

*Primary Examiner* — Eduardo C Robert
*Assistant Examiner* — Christina Negrellirodriguez
(74) *Attorney, Agent, or Firm* — Locke Lord LLP; Scott D. Wofsy

(57) ABSTRACT

A cannula assembly for use in robotic surgery is disclosed that includes a robotic cannula having a housing with an open end and a tubular portion extending distally from the housing, the tubular portion being dimensioned to accommodate passage of a surgical instrument having a 12 mm diameter, an adapter assembly configured for engagement within the open end of the cannula housing and including a tubular body with a passage supporting a primary seal dimensioned to accommodate passage of a surgical instrument having a 12 mm diameter, and an insert tube dimensioned to extend through the passage of the body portion of the adapter assembly and the tubular portion of the robotic cannula, the insert tube including a head portion with a passage supporting a secondary seal dimensioned to accommodate a surgical instrument having an 8 mm diameter.

16 Claims, 5 Drawing Sheets

(51) Int. Cl.
        *A61B 17/00*      (2006.01)
        *A61B 34/00*      (2016.01)
        *A61B 34/30*      (2016.01)
(52) U.S. Cl.
        CPC ...... *A61B 17/3423* (2013.01); *A61B 17/3462* (2013.01); *A61M 13/003* (2013.01); *A61B 34/30* (2016.02); *A61B 34/70* (2016.02); *A61B 2017/00477* (2013.01); *A61B 2017/00486* (2013.01)
(58) Field of Classification Search
        CPC ........ A61B 2017/3445; A61B 17/3462; A61B 17/3421–2017/3452
        USPC .................................................. 600/204–205
        See application file for complete search history.

(56) References Cited

U.S. PATENT DOCUMENTS

| | | |
|---|---|---|
| 2014/0357958 A1 | 12/2014 | Eltoft et al. |
| 2015/0005583 A1* | 1/2015 | Davis ................. A61B 17/3423 600/204 |
| 2015/0173792 A1 | 6/2015 | McGinley et al. |

OTHER PUBLICATIONS

Office Action issued in corresponding Korean Patent Application No. KR 10-2019-7003951, dated Sep. 10, 2020.
Korean Office Action dated Feb. 2, 2021, issued during the prosecution of Korean Patent Application No. KR 10-2019-7003951.

* cited by examiner

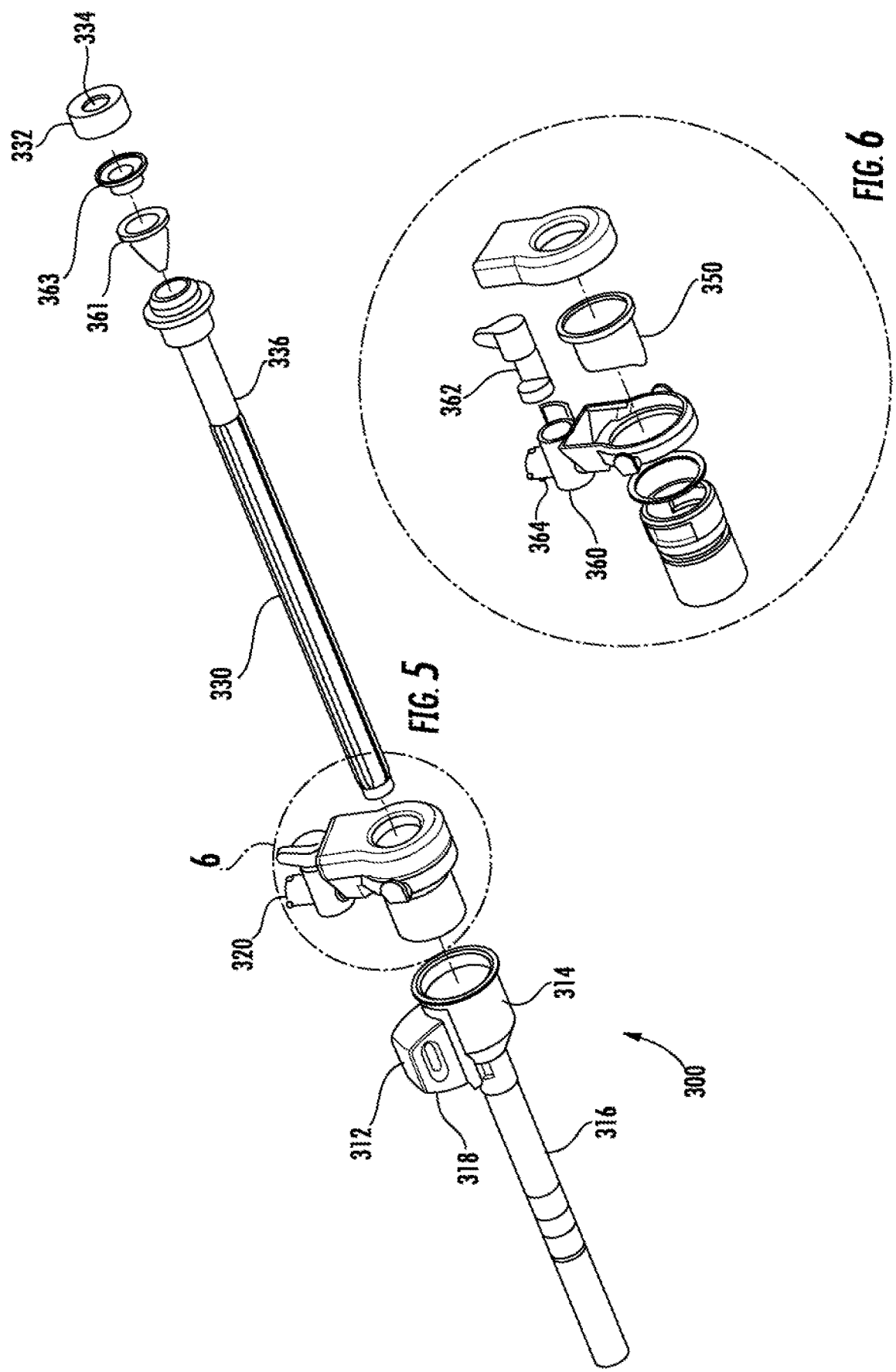

CANNULA ASSEMBLY FOR ROBOTICALLY ASSISTED PRESSURE REGULATED LAPAROSCOPIC SURGICAL PROCEDURES

CROSS-REFERENCE TO RELATED APPLICATION

The subject invention claims the benefit of priority from U.S. Provisional Patent Application 62/360,724 filed Jul. 11, 2016, the disclosure of which is herein incorporated by reference in its entirety.

BACKGROUND OF THE INVENTION

1. Field of the Invention

The subject invention is directed to laparoscopic surgery, and more particularly, to a cannula assembly for use during robotically assisted, pressure regulated laparoscopic surgical procedures to accommodate instruments of different size.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a surgical access device (sometimes referred to as a "cannula" or "trocar") equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar.

Trocars having different working diameters are also employed during laparoscopic procedures to accommodate different sized instruments. For example, it may be appropriate to use a 12 mm cannula for a surgical stapling device, while an 8 mm trocar may be more appropriate for a grasping instrument.

It would be beneficial therefore, to provide a single trocar assembly that can be used for differently sized instruments so as to avoid having to use different sized trocars, requiring multiple separate incisions. Moreover, it would be beneficial to provide such a trocar that is uniquely designed for use in robotically assisted laparoscopic surgical procedures, which have become prevalent. Such a trocar typically includes exterior structure that can be engaged or otherwise gripped by a robotic manipulator.

SUMMARY OF THE INVENTION

The subject invention is directed to a new and useful cannula assembly for use in robotically assisted, pressure regulated laparoscopic surgery. More particularly, the cannula assembly of the subject invention is adapted and configured for use in conjunction with the da Vinci Surgical System, which his manufactured by Intuitive Surgical, Inc., of Sunnyvale, Calif., which is a tool that utilizes advanced, robotic technologies to assist a surgeon in performing minimally invasive surgical procedures within the abdominal cavity of a patient.

The da Vinci Surgical System has a 3D high definition (3D-HD) vision system, special instruments and computer software that allow a surgeon to operate with enhanced vision, precision, dexterity and control. The 3D-HD image can be magnified up to 10 times so the surgeon has a close-up view of the area he or she is operating on. The da Vinci instruments have mechanical wrists that bend and rotate to mimic the movements of the human wrist—allowing the surgeon to make small, precise movements inside the patient's body. The da Vinci software can minimize the effects of a surgeon's hand tremors on instrument movements.

The cannula assembly of the subject invention includes a cannula having a proximal housing portion with an open end and an elongated tubular portion extending distally from the proximal housing portion. The assembly further includes an adapter configured for reception within the open end of the proximal housing portion of the cannula and including a tubular body with a central passage supporting a main seal. In addition, the assembly includes an insert tube that is dimensioned and configured to extend through the central passage of the body portion of the adapter and the tubular portion of the cannula, wherein the insert tube includes a proximal head portion with a central passage supporting a duckbill seal.

The adapter includes an upper housing for supporting the main seal within the central passage of the tubular body of the adapter. A connector port extends from the upper housing of the adapter for connecting the adapter to a gas delivery tube. A toggle valve is operatively associated with the connector port for controlling the flow of gas to the adapter. In addition, a clamping collar is operatively associated with the upper housing of the adapter for releasably securing the adapter to the proximal housing portion of the cannula.

An O-ring seal surrounds the tubular body portion of the adapter below the upper housing for sealingly engaging an interior surface of the proximal housing portion of the cannula. A flat seal is supported within the central passage of the proximal head portion of the insert tube. The flat seal is positioned distal to the secondary duckbill seal. An insert cover encloses the duckbill seal and flat seal within the head portion of the insert tube.

Preferably, the central passage of the tubular body portion of the adapter is dimensioned and configured to accommodate a surgical instrument having a 12 mm outer diameter, and the central passage of the head portion of the insert tube is dimensioned and configured to accommodate a surgical instrument having an 8 mm outer diameter.

These and other features of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the robotic cannula assembly of the subject invention without undue experimentation, preferred embodiments thereof will be described in detail herein below with reference to certain figures, wherein:

FIG. 5 is an exploded perspective view of yet another embodiment of the cannula assembly of the subject invention, which includes a robotic cannula portion having a 12 mm working diameter, an adapter assembly configured for reception in the housing of the robotic cannula portion, and an insert tube having an 8 mm working diameter, and wherein the adapter assembly has a proprietary tube fitting with camming lugs for engaging a tube connector; and FIG. 6 is an exploded perspective view of the adapter assembly shown in FIG. 5 with parts separated for ease of illustration.

DETAILED DESCRIPTION OF PREFERRED EMBODIMENTS

Figure 1:
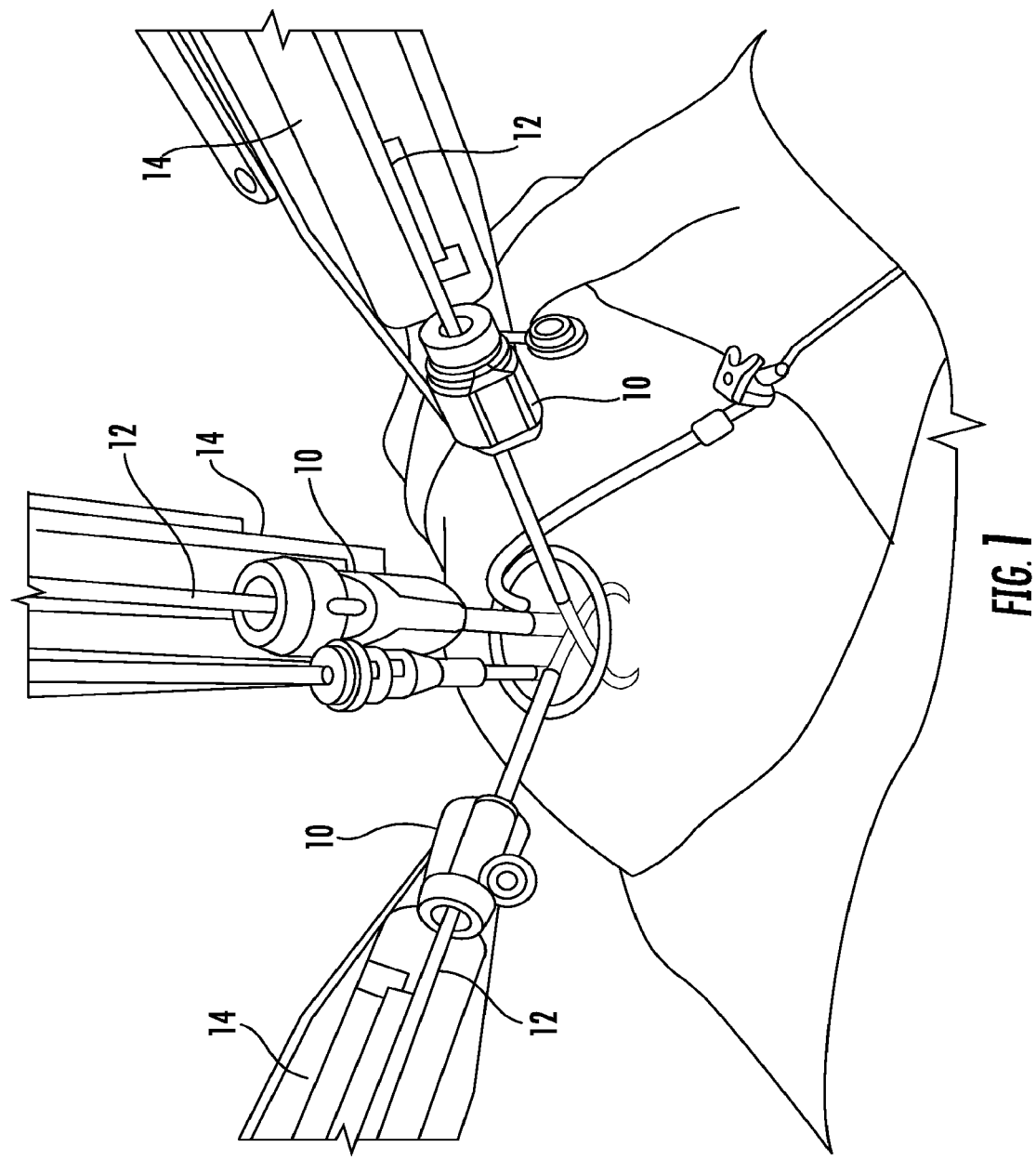
FIG. 1 is an illustration of a robotically assisted laparoscopic surgical procedure involving a plurality of robotic cannula devices.

Referring now to the drawings wherein like reference numerals identify similar structural features and/or elements of the subject matter disclosed herein, there is illustrated in FIG. 1 an illustration of a robotically assisted laparoscopic surgical procedure involving a plurality of access devices or cannulas 10 which provide access for surgical instrumentation 12 controlled by robotic manipulators 14. More particularly, the robotic manipulators 14 are part of a system such as the da Vinci Surgical System, which is manufactured by Intuitive Surgical, Inc., of Sunnyvale, Calif., or a similar robotic surgical system.

Figure 2:
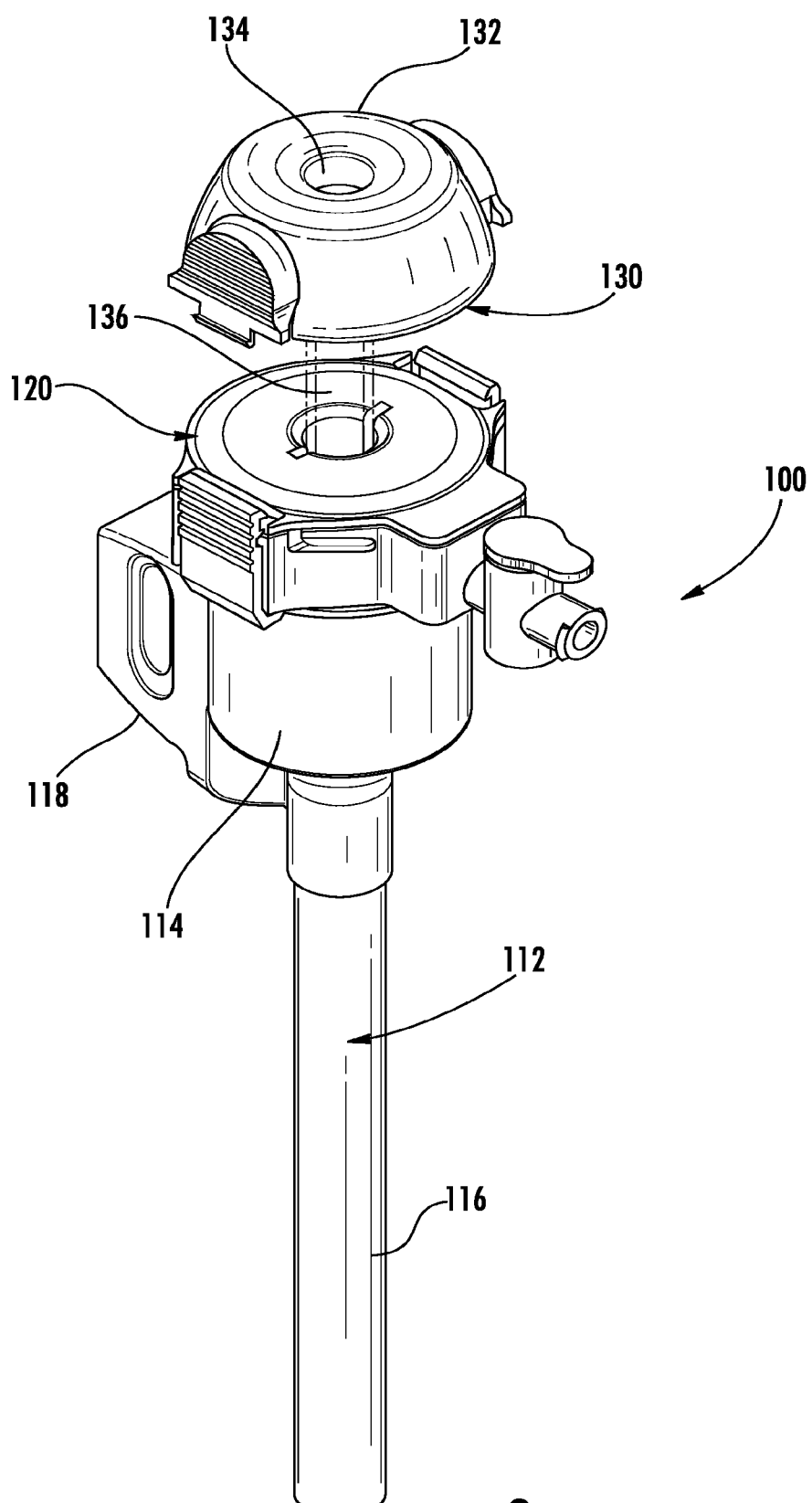
FIG. 2 is a perspective view of an embodiment of the cannula assembly of the subject invention, which includes a robotic cannula portion having a 12 mm working diameter, an adapter assembly configured for reception in the housing of the robotic cannula, and an insert tube in a partially inserted positon relative to the adapter assembly which has an 8 mm working diameter, and wherein the adapter assembly has a conventional luer fitting for engaging a tube connector.

Referring now to FIG. 2, there is illustrated a cannula assembly constructed in accordance with a preferred embodiment of the subject invention and designated generally by reference numeral 100. Cannula assembly 100 is particularly adapted and configured for use in robotically assisted, pressure regulated laparoscopic surgery, involving, for example, the da Vinci Surgical System.

Cannula assembly 100 includes a robotic cannula portion 112 having a proximal housing portion 114 with an open end and a distally extending tubular body 116, which has a 12 mm working diameter, i.e., the tubular body portion is dimensioned and configured to accommodate a surgical instrument having a 12 mm outer diameter. The housing portion 114 includes an engagement flange 118 configured to be selectively engaged by a robotic manipulator 14, for use as shown for example in FIG. 1. Cannula assembly 100 further includes an adapter assembly 120 configured for reception in the proximal housing portion 114 of the robotic cannula portion 112, and a separable insert tube 130 which has an upper cap 132 with an access port 134 and a distally extending tubular body portion 136 having an 8 mm working diameter, i.e. the tubular body portion 136 is dimensioned and configured to accommodate a surgical instrument having an 8 mm outer diameter. The tubular body portion 136 is configured to extend through the central passage of the tubular body 144 of the adapter assembly 120 and the tubular body 116 of the robotic cannula portion 112. A mechanical seal, such as for example, a duckbill seal or the like, is associated with the access port 134 to support a secondary seal for sealed access to the tubular body portion 136 for an 8 mm surgical instrument. While it is not shown in this embodiment, this seal is shown in the embodiments illustrated in FIGS. 3 and 6, e.g., seals 150 and 350.

Figure 3:
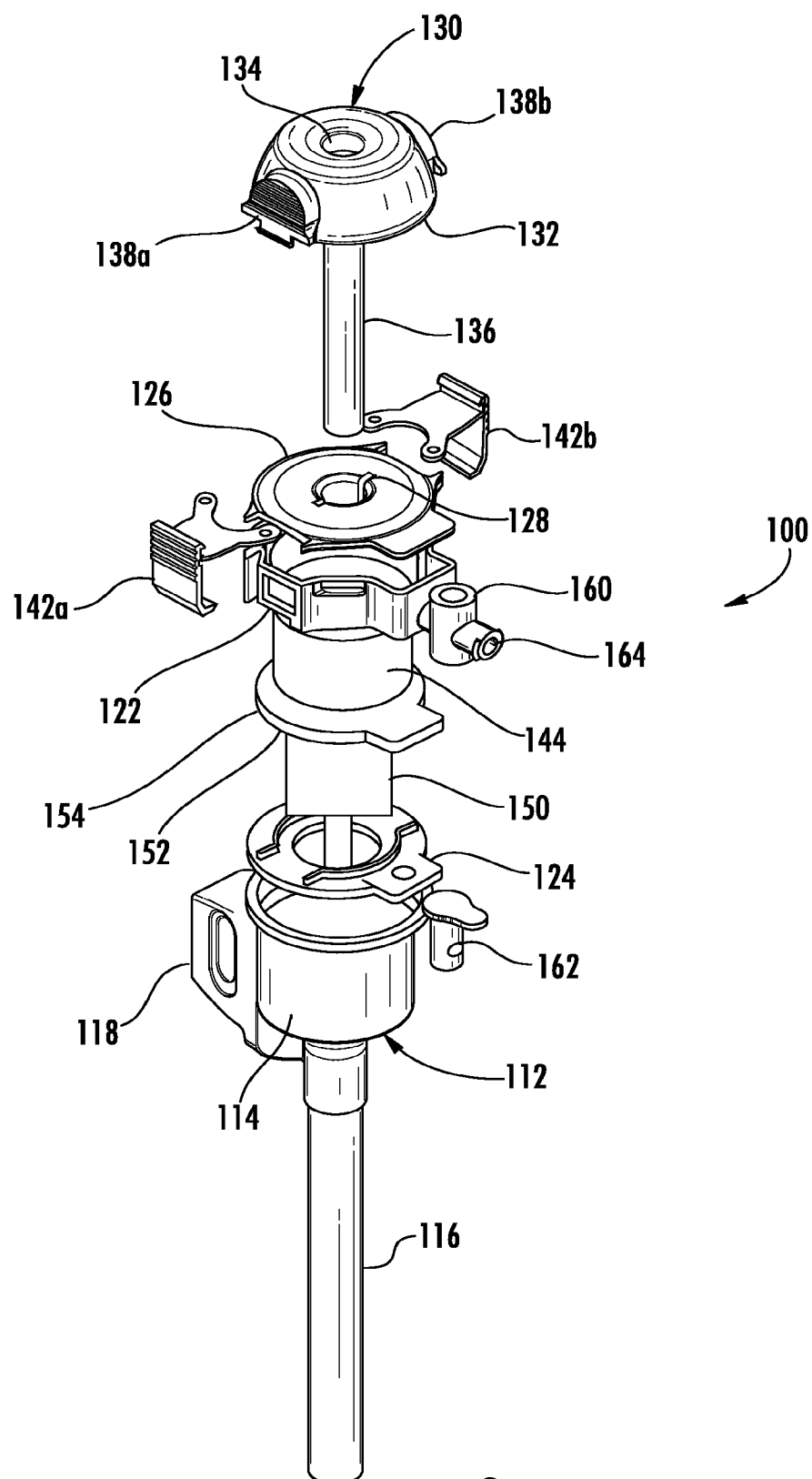
FIG. 3 is an exploded perspective view of the cannula assembly of FIG. 2, with parts separated for ease of illustration.

Referring now to FIG. 3, the adapter assembly 120 is configured for reception within the open end of the proximal housing portion 114 and includes an upper housing 122 and a lower housing 124. The upper housing 122 includes a cover 126 that defines an access port 128 for receiving a 12 mm instrument as well as the tubular portion 136 of insert tube 130. The cover 126 encloses a pair of diametrically opposed latches 142a and 142b which form a clamping collar operatively associated with the upper housing 122 for releasably securing the adapter assembly 120 to the open end of the proximal housing portion 114 and which interact with corresponding diametrically opposed locking tabs 138a and 138b on the upper cap 132 of insert 130 for selectively securing the insert tube 130 to the adapter assembly 120 during use.

The upper housing 122 of the adapter assembly 120 further includes a tubular body 144 with a central passage that supports, encloses or otherwise houses a primary seal 150. In this embodiment, the primary seal assembly 150 includes a four-part double lipped duckbill seal, for example, and can include a main seal above the duckbill seal. The primary seal 150 includes an upper flange portion 152 that is dimensioned and configured to be captured and retained between the upper and lower housing 122 and 124 of the adapter assembly 120 and more particularly between the top of the tubular body 144 and the bottom of lower housing 124 which seats opposite the cover 126 inside the upper housing 122 as oriented in FIG. 3. The tubular body 144 supports an O-ring seal 154 that functions to seal the interface between the inner diameter of the open end of the proximal housing 114 of the robotic cannula portion 112 and the outer diameter of the tubular body 144 of the of the adapter assembly 120.

The upper housing 122 of the adapter assembly 120 also includes a valve assembly 160 that includes a rotatable toggle valve stem 162 and an inlet port 164 in the form of a luer lock connection port extending from the adapter assembly 120. Those skilled in the art will readily appreciate that any other suitable type of connection port can be used. This port is configured to connect with a gas delivery tube that could be associated with a source of insufflation gas.

Figure 4:
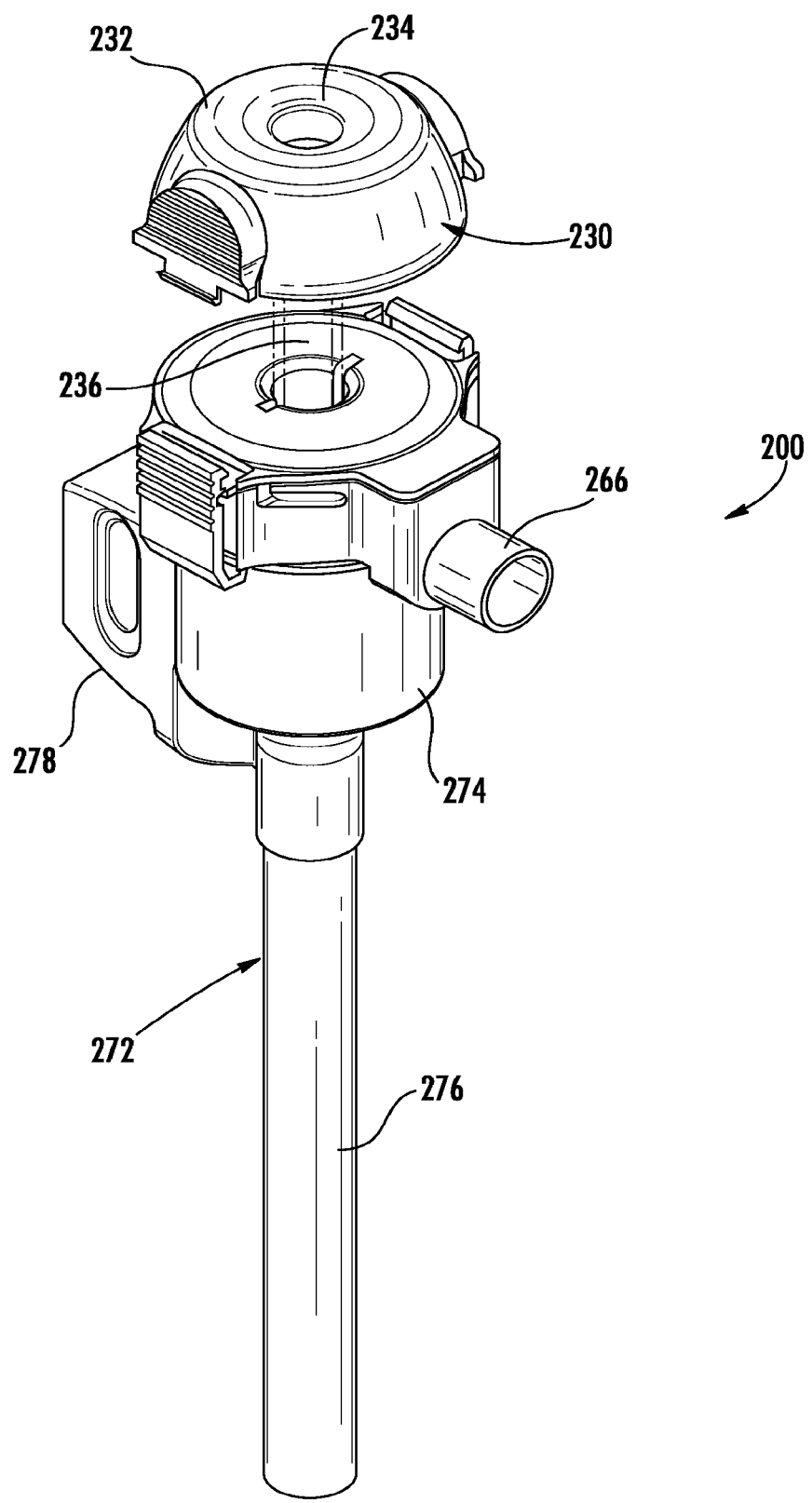
FIG. 4 is a perspective view of another embodiment of the cannula assembly of the subject invention, which includes a robotic cannula portion having a 12 mm working diameter, an adapter assembly configured for reception in the housing of the robotic cannula portion, and an insert tube in a partially inserted positon relative to the adapter assembly which has an 8 mm working diameter, and wherein the adapter assembly has a proprietary tube fitting with camming lugs for engaging a tube connector.

Referring now to FIG. 4, there is illustrated another cannula assembly constructed in accordance with a preferred embodiment of the subject invention and designated generally by reference numeral 200. Cannula assembly 200 is substantially similar to cannula assembly 100 in that it includes a robotic cannula portion 272 having a proximal housing portion 274 and a distally extending tubular body portion 276, which has a 12 mm working diameter. The housing portion 274 includes an engagement flange 278 configured to be selectively engaged by a robotic manipulator 14, for use as shown in FIG. 1.

Cannula assembly 200 further includes an adapter assembly 220 configured for reception in the proximal housing portion 274 of the robotic cannula portion 272, and a separable insert tube 230 which has an upper cap 232 with an access port 234 and a distally extending tubular body portion 236 having an 8 mm working diameter.

Cannula assembly 200 differs from cannula assembly 100 in that the valve assembly 260 that includes an over-sized inlet port 164 with unique proprietary configuration that includes a plurality of circumferentially spaced apart camming lugs 266 for engagement with a proprietary coupling, such as for example, the type of coupling disclosed in commonly assigned U.S. Patent Application Publication No. 2014/0171855, and its progeny, which are incorporated herein by reference in their entirety.

Referring now to FIGS. 5 and 6, there is illustrated another embodiment of the cannula assembly of the subject invention, which is designated generally by reference numeral 300. As illustrated, cannula assembly 300 includes a robotic cannula portion 312 having a proximal housing portion 314 and a distally extending tubular body portion 316, which has a 12 mm working diameter. The proximal housing portion 314 includes an engagement flange 318 configured to be selectively engaged by a robotic manipulator 14, for use as shown in FIG. 1.

Cannula assembly 300 further includes an adapter assembly 320 configured for reception in the proximal housing portion 314 of the robotic cannula portion 312, and a separable insert tube 330 which has an upper cover 332 with an access port 334 and a distally extending tubular body portion 336 having an 8 mm working diameter. The adapter assembly 320, which is best seen in FIG. 6, includes a 12 mm two-part single lipped duckbill seal 350 and a valve assembly 360 that includes an over-sized toggle valve 362 and inlet port 364 with a unique proprietary configuration. The insert tube 330 also includes an 8 mm duckbill seal 361 and a secondary 8 mm flat seal 363 supported within the central passage or access port 334 of the upper cup or cover 332 of the tube insert 330 for sealed access into the tubular portion 336. The flat seal 363 is positioned proximal to the duckbill seal 361. The upper cover 332 encloses the duckbill seal 361 and flat seal 363 within a proximal head portion of the insert tube 330.

While the subject invention has been shown and described with reference to preferred embodiments, those skilled in the art will readily appreciate that various changes and/or modifications may be made thereto without departing from the scope of this disclosure.

What is claimed is:

1. A cannula assembly for use in robotically assisted laparoscopic surgery, comprising:
    a) an adapter assembly configured for reception within an open end of a proximal housing portion of a robotic cannula and including a tubular body with a central passage supporting a primary seal; and
    b) an insert tube dimensioned and configured to extend through the central passage of the tubular body of the adapter assembly and a tubular portion of the robotic cannula portion, the insert tube extending distally and including a proximally extending upper cup with an access port supporting a secondary seal, wherein the adapter assembly includes an upper housing extending in a proximal direction, wherein the tubular body extends in a distal direction from the upper housing for supporting the primary seal within the central passage of the tubular body of the adapter assembly, and wherein an inlet port extends laterally from the upper housing of the adapter assembly for connecting the adapter assembly to a gas delivery tube, wherein the inlet port is in direct fluid communication through the adapter assembly with an interior portion of the upper housing that is proximal relative to the primary seal, without the primary seal intervening between the inlet port and the interior portion of the upper housing.

2. The cannula assembly of claim 1, wherein a toggle valve is operatively associated with the inlet port for controlling the flow of gas to the adapter assembly.

3. The cannula assembly of claim 1, wherein a flat seal is supported within a central passage of the upper cup of the insert tube.

4. The cannula assembly of claim 3, wherein the flat seal is positioned proximal to the secondary seal.

5. The cannula assembly of claim 1, wherein a flat seal is supported within a central passage of the upper cup of the insert tube, further comprising an upper cover for enclosing the secondary seal and flat seal within a proximal head portion of the insert tube.

6. The cannula assembly of claim 1, wherein the central passage of the tubular body portion of the adapter assembly is dimensioned and configured to accommodate a surgical instrument having a 12 mm outer diameter, and the access port of the upper cup of the insert tube is dimensioned and configured to accommodate a surgical instrument having an 8 mm outer diameter.

7. A cannula assembly for use in robotically assisted laparoscopic surgery, comprising:
    a) an adapter assembly configured for reception within an open end of a proximal housing portion of a robotic cannula and including a tubular body with a central passage supporting a primary seal; and
    b) an insert tube dimensioned and configured to extend through the central passage of the tubular body of the adapter assembly and a tubular portion of the robotic cannula portion, the insert tube extending distally and including a proximally extending upper cup with an access port supporting a secondary seal, wherein the adapter assembly includes an upper housing extending in a proximal direction, wherein the tubular body extends in a distal direction from the upper housing for supporting the primary seal within the central passage of the tubular body of the adapter assembly, further comprising a clamping collar operatively associated with the upper housing of the adapter assembly for releasably securing the adapter assembly to a proximal housing portion of the robotic cannula, and wherein an inlet port extends laterally from the upper housing of the adapter assembly for connecting the adapter assembly to a gas delivery tube, wherein the inlet port is in direct fluid communication through the adapter assembly with an interior portion of the upper housing that is proximal relative to the primary seal, without the primary seal intervening between the inlet port and the interior portion of the upper housing.

8. A cannula assembly for use in robotically assisted laparoscopic surgery, comprising:
   a) an adapter assembly configured for reception within an open end of a proximal housing portion of a robotic cannula and including a tubular body with a central passage supporting a primary seal; and
   b) an insert tube dimensioned and configured to extend through the central passage of the tubular body of the adapter assembly and a tubular portion of the robotic cannula portion, the insert tube extending distally and including a proximally extending upper cup with an access port supporting a secondary seal, wherein the adapter assembly includes an upper housing extending in a proximal direction, wherein the tubular body extends in a distal direction from the upper housing for supporting the primary seal within the central passage of the tubular body of the adapter assembly, further comprising an O-ring seal surrounding the tubular body portion of the adapter assembly below the upper housing for sealingly engaging an interior surface of a proximal housing portion of the robotic cannula, and wherein an inlet port extends laterally from the upper housing of the adapter assembly for connecting the adapter assembly to a gas delivery tube, wherein the inlet port is in direct fluid communication through the adapter assembly with an interior portion of the upper housing that is proximal relative to the primary seal, without the primary seal intervening between the inlet port and the interior portion of the upper housing.

9. A cannula assembly for use in robotically assisted laparoscopic surgery, comprising:
   a) an adapter assembly configured for reception within an open end of a proximal housing portion of a robotic cannula and including a tubular body with a central passage supporting a primary seal; and
   b) an insert tube dimensioned and configured to extend through the central passage of the tubular body of the adapter assembly and a tubular portion of the robotic cannula portion, the insert tube extending distally and including a proximally extending upper cup with an access port supporting a secondary seal, and further comprising a robotic cannula portion having a proximal housing portion with an open end and an elongated tubular portion extending distally from the proximal housing portion, and wherein an inlet port extends laterally from an upper housing of the adapter assembly for connecting the adapter assembly to a gas delivery tube, wherein the upper housing extends in a proximal direction, wherein the tubular body extends in a distal direction from the upper housing, wherein the inlet port is in direct fluid communication through the adapter assembly with an interior portion of the upper housing that is proximal relative to the primary seal, without the primary seal intervening between the inlet port and the interior portion of the upper housing.

10. A cannula assembly for use in robotically assisted laparoscopic surgery, comprising:
   a) a robotic cannula portion having a proximal housing portion with an open end and an elongated tubular body portion extending distally from the proximal housing portion, the tubular body portion of the cannula being dimensioned and configured to accommodate passage of a surgical instrument having a 12 mm outer diameter;
   b) an adapter assembly configured for releasable engagement within the open end of the proximal housing portion of the cannula and including a tubular body portion with a central passage supporting a primary seal dimensioned to accommodate passage of a surgical instrument having a 12 mm outer diameter, wherein the adapter assembly includes an upper housing for supporting the primary seal within the central passage of the tubular body of the adapter assembly and wherein an inlet port extends laterally from the upper housing of the adapter assembly for connecting the adapter assembly to a gas delivery tube, wherein the upper housing extends in a proximal direction, wherein the tubular body extends in a distal direction from the upper housing, wherein the inlet port is in direct fluid communication through the adapter assembly with an interior portion of the upper housing that is proximal relative to the primary seal, without the primary seal intervening between the inlet port and the interior portion of the upper housing; and
   c) an insert tube dimensioned and configured to extend through the central passage of the tubular body portion of the adapter assembly and the tubular body portion of the robotic cannula, the insert tube extending distally and including a proximally extending upper cup with an access port supporting a secondary seal dimensioned and configured to accommodate a surgical instrument having an 8 mm outer diameter.

11. The cannula assembly of claim 10, wherein a toggle valve is operatively associated with the inlet port for controlling the flow of gas to the adapter assembly.

12. The cannula assembly of claim 10, further comprising a clamping collar operatively associated with the upper housing of the adapter assembly for releasably securing the adapter assembly to a proximal housing portion of the robotic cannula.

13. The cannula assembly of claim 10, further comprising an O-ring seal surrounding the tubular body portion of the adapter assembly below the upper housing for sealingly engaging an interior surface of the proximal housing portion of the robotic cannula.

14. The cannula assembly of claim 10, wherein a flat seal is supported within the central passage of the upper cup of the insert tube.

15. The cannula assembly of claim 14, wherein the flat seal is positioned proximal to the secondary seal.

16. The cannula assembly of claim 5, further comprising an upper cover for enclosing the secondary seal and flat seal within a proximal head portion of the insert tube.

* * * * *